US012453650B2

(12) United States Patent
Woods

(10) Patent No.: US 12,453,650 B2
(45) Date of Patent: Oct. 28, 2025

(54) FACIAL WARMING DEVICE

(71) Applicant: Markiese Woods, Attalla, AL (US)

(72) Inventor: Markiese Woods, Attalla, AL (US)

( * ) Notice: Subject to any disclaimer, the term of this patent is extended or adjusted under 35 U.S.C. 154(b) by 329 days.

(21) Appl. No.: 18/206,818

(22) Filed: Jun. 7, 2023

(65) Prior Publication Data

US 2024/0407943 A1 Dec. 12, 2024

(51) Int. Cl.
*A61F 7/00* (2006.01)

(52) U.S. Cl.
CPC ...... *A61F 7/007* (2013.01); *A61F 2007/0013* (2013.01)

(58) Field of Classification Search
CPC .............. A61F 7/007; A61F 2007/0003; A61F 2007/0015; A61F 2007/0013; A61F 2007/0014
See application file for complete search history.

(56) References Cited

U.S. PATENT DOCUMENTS

| | | | | |
|---|---|---|---|---|
| 2,038,275 | A | 4/1936 | Fogg | |
| D745,693 | S | 12/2015 | Burgess | |
| 9,795,502 | B1 | 10/2017 | Kopes | |
| 10,314,737 | B2 | 6/2019 | Loeffler | |
| 11,045,386 | B2 | 6/2021 | Oda | |
| 11,135,087 | B2 | 10/2021 | Sitt | |
| 12,337,175 | B2 * | 6/2025 | Kim | A61N 1/36021 |
| 2008/0161892 | A1 | 7/2008 | Mercuro | |
| 2012/0022411 | A1 * | 1/2012 | Wu | A61N 1/046 601/15 |
| 2019/0336787 | A1 * | 11/2019 | Kweon | A45D 44/002 |
| 2020/0268550 | A1 * | 8/2020 | Mehta | A61F 7/02 |
| 2021/0106460 | A1 * | 4/2021 | Fan | A61F 7/00 |
| 2024/0115419 | A1 * | 4/2024 | Mehta | A61F 7/007 |

FOREIGN PATENT DOCUMENTS

| | | | | |
|---|---|---|---|---|
| EP | 3804668 | A1 * | 4/2021 | A61F 7/007 |
| GB | 1038891 | | 8/1966 | |
| WO | WO-2020251177 | A1 * | 12/2020 | A61F 7/02 |
| WO | WO-2022158781 | A1 * | 7/2022 | A61H 39/002 |
| WO | WO-2023095976 | A1 * | 6/2023 | A61F 7/007 |

* cited by examiner

*Primary Examiner* — Joseph A Stoklosa

(57) ABSTRACT

A facial warming device for treating dental pain with heat includes a mask that is wearable on a user's face. The mask has a nose that is centrally positioned between a plurality of straps. A plurality of heating elements is each integrated into the mask to facilitate dental pain to be treated with heat. Each of the plurality of heating elements is independently actuatable with respect to each other to apply heat to specific areas of the users' jaw for treating localized dental pain. A communication unit is positionable in a pocket on the mask. The communication unit is in communication with each of the plurality of heating elements and a personal electronic device to facilitate the personal electronic device to remotely control the plurality of heating elements.

11 Claims, 5 Drawing Sheets

FACIAL WARMING DEVICE

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to warming devices and more particularly pertains to a new warming device for treating dental pain with heat. The device includes a mask that is wearable on a user's face and a plurality of heating elements integrated into the mask. Each of the plurality of heating elements is independently actuatable for warming selected sides of the user's jaw. In this way heat can be applied to the user's jaw to treat localized dental pain. The device includes a communication unit that is in wireless communication with a personal electronic device to facilitate the heating elements to be remotely controlled with the personal electronic device.

(2) Description of Related Art Including Information Disclosed Under 37 CFR 1.97 and 1.98

The prior art relates to warming devices including a variety of face masks that have eye holes to accommodate a user's eyes and heating elements in the face mask and a variety of face masks that are structured to curved around the user's jaw. In no instance does the prior art disclose a mask that is wearable on a user's face which has a plurality of heating elements that are independently actuatable and which are remotely controlled with a personal electronic device.

BRIEF SUMMARY OF THE INVENTION

An embodiment of the disclosure meets the needs presented above by generally comprising a mask that is wearable on a user's face. The mask has a nose that is centrally positioned between a plurality of straps. A plurality of heating elements is each integrated into the mask to facilitate dental pain to be treated with heat. Each of the plurality of heating elements is independently actuatable with respect to each other to apply heat to specific areas of the users' jaw for treating localized dental pain. A communication unit is positionable in a pocket on the mask. The communication unit is in communication with each of the plurality of heating elements and a personal electronic device to facilitate the personal electronic device to remotely control the plurality of heating elements.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
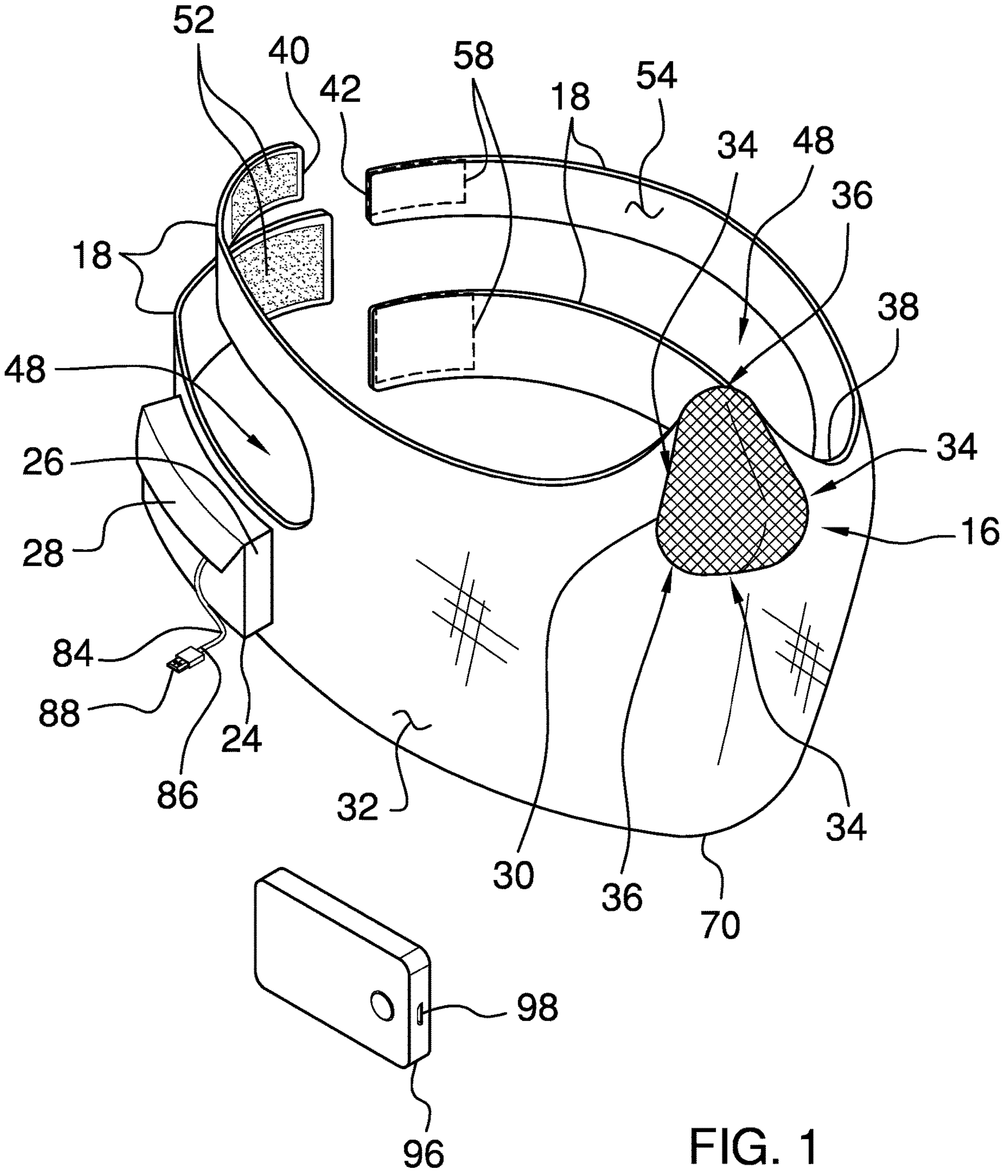
FIG. 1 is a front perspective view of a facial warming device according to an embodiment of the disclosure.
Figure 2:
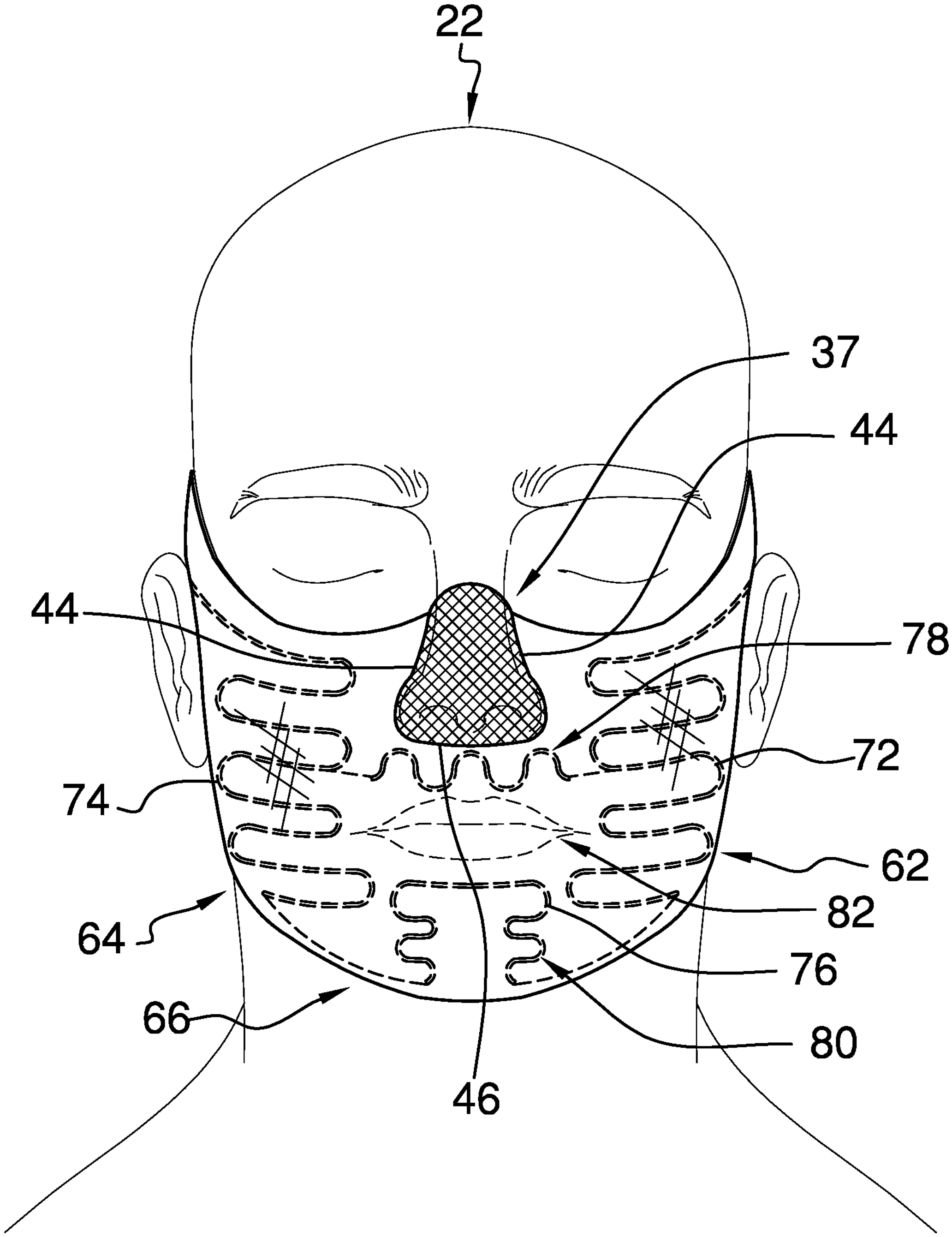
FIG. 2 is a phantom in-use view of an embodiment of the disclosure.
Figure 3:
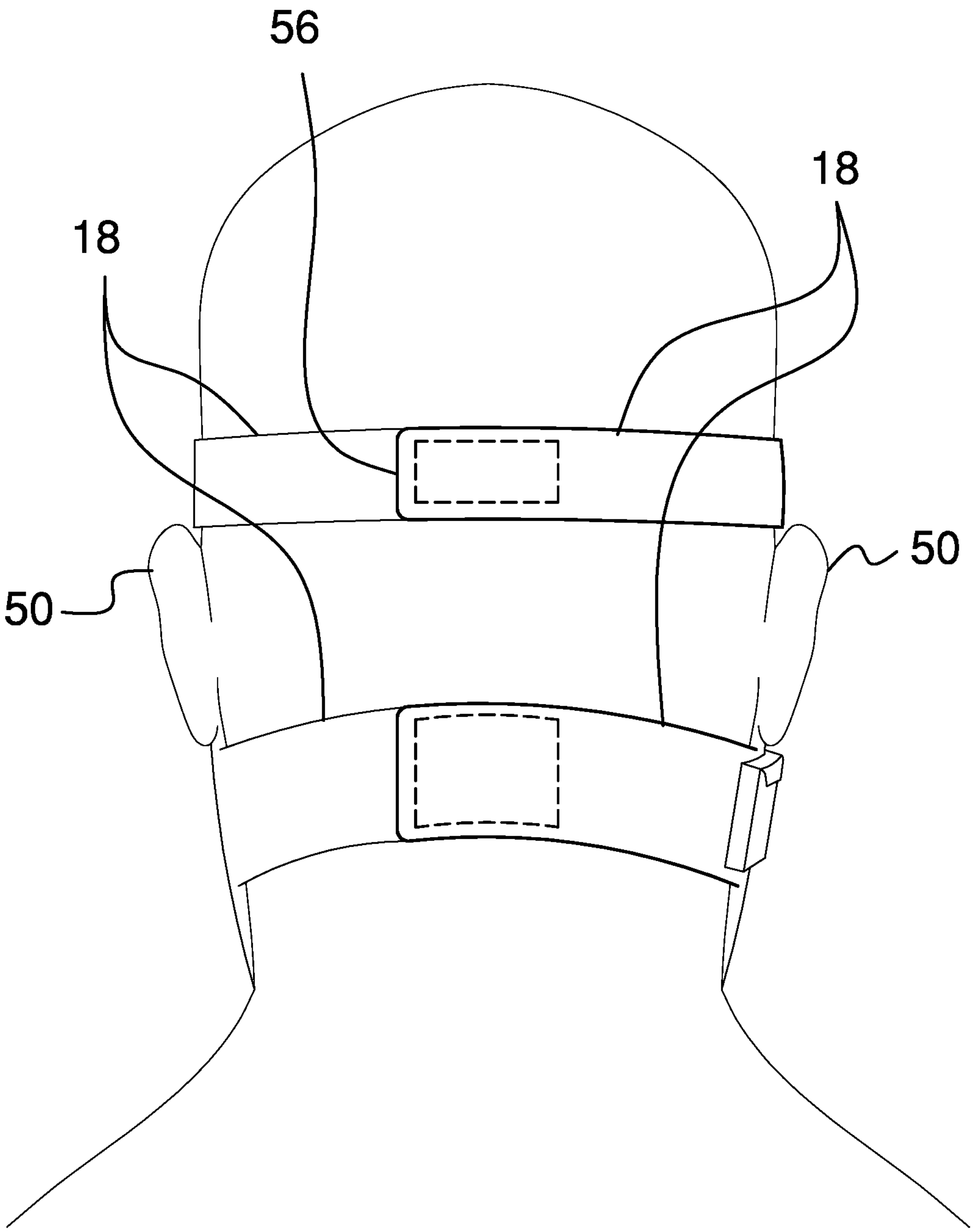
FIG. 3 is a back in-use view of an embodiment of the disclosure.
Figure 4:
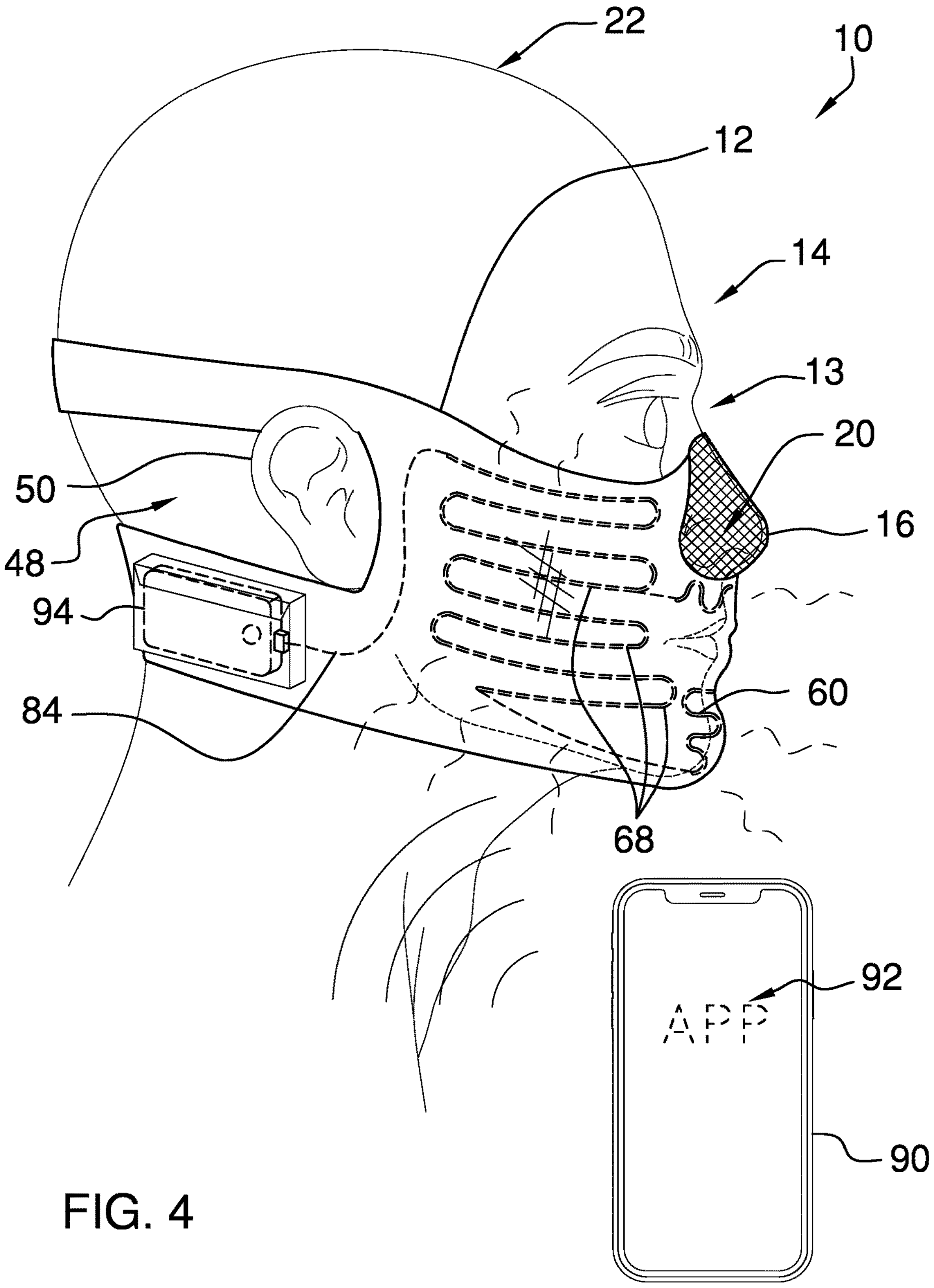
FIG. 4 is a phantom perspective in-use view of an embodiment of the disclosure.
Figure 5:
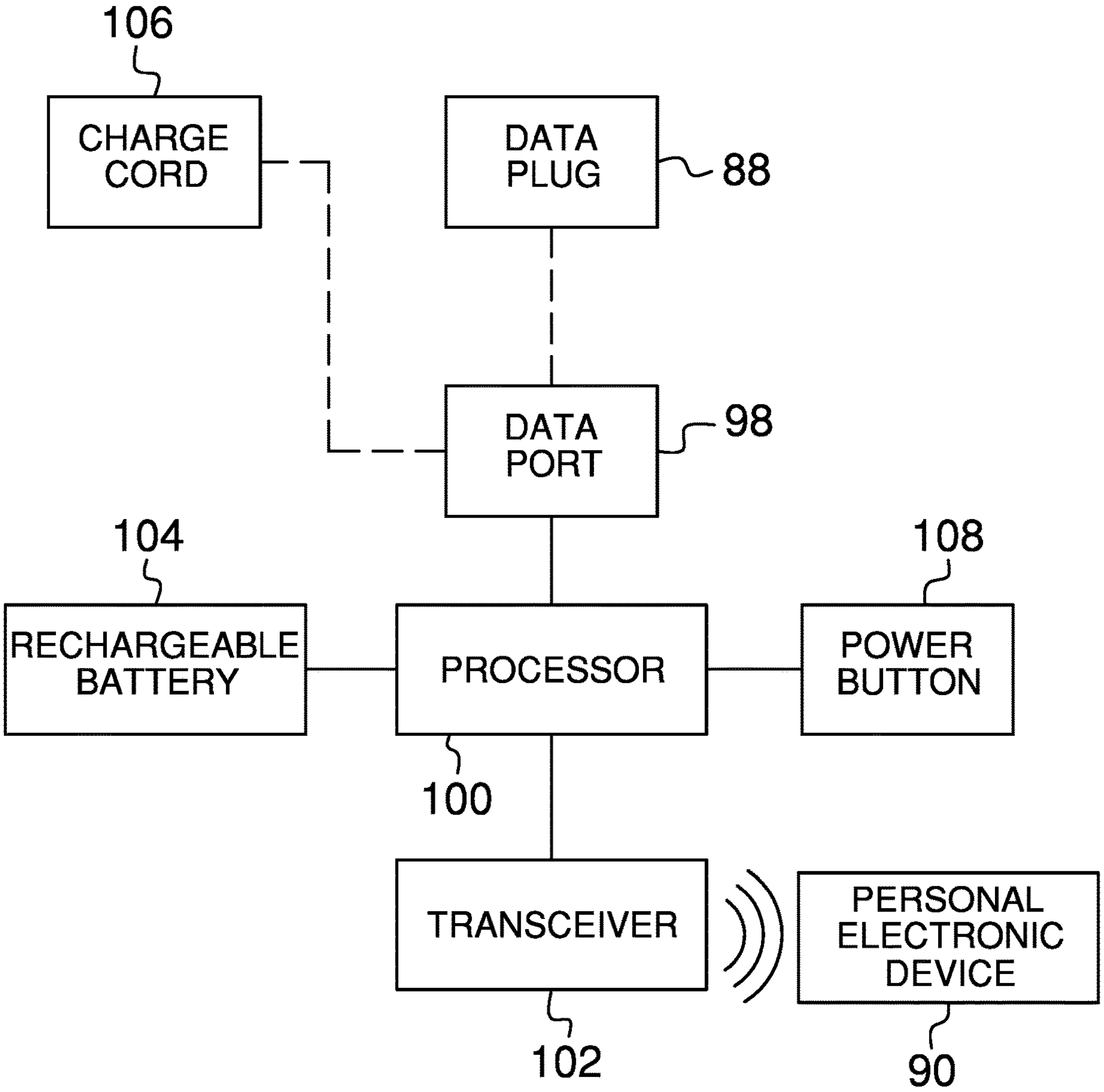
FIG. 5 is a schematic view of an embodiment of the disclosure.

With reference now to the drawings, and in particular to FIGS. 1 through 5 thereof, a new warming device embodying the principles and concepts of an embodiment of the disclosure and generally designated by the reference numeral 10 will be described.

As best illustrated in FIGS. 1 through 5, the facial warming device 10 generally comprises a mask 12 that is wearable on a face 13 of a user 14. The mask 12 has a nose 16 that is centrally positioned between a plurality of straps 18; the nose 16 on the mask 12 covers the user's nose 20 and each of the straps 18 extends around the user's head 22. The mask 12 has a pocket 24 is attached to the mask 12; said pocket 24 has a top end 26 that is open into an interior of the pocket 24 and a flap 28 that is foldable over the top end 26 of the pocket 24. The nose 16 has a perimeter edge 30 that is attached to an outwardly facing surface 32 of the mask 12 and the perimeter edge 30 has a plurality of sides 34 intersecting each other at a curve 36 such that the nose 16 has the shape of a reuleaux triangle 37.

The nose 16 curves outwardly from the outwardly facing surface 32 to accommodate the user's nose 20. The nose 16 extends downwardly from a top edge 38 of the mask 12 at a point that is centrally located between a first lateral edge 40 and a second lateral edge 42 of the mask 12. Additionally, the top edge 38 curves upwardly along each of a pair of legs 44 of the reuleaux triangle 37 having a base 46 of the reuleaux triangle 37 being spaced downwardly from the top edge 38. The nose 16 is comprised of a mesh material to facilitate the user 14 to breathe through the nose 16 when the user 14 is wearing the mask 12. Furthermore, the mask 12 is comprised of an elastomeric and thermally insulating material, including but not being limited to, fleece cloth or neoprene.

The mask 12 has a pair of slots 48 each extending from a respective one of the first lateral edge 40 and the second lateral edge 42 of the mask 12 toward the nose 16. Each of the slots 48 is centrally positioned along the respective first lateral edge 40 and the second lateral edge 42 such that each of the slots 48 defines a respective pair of the plurality of straps 18. In this way each of the pair of slots 48 can accommodate a respective one of the user's ears 50 when the straps 18 are wrapped around the user's head 22. A pair of first fasteners 52 is provided and each of the first fasteners 52 is attached to an inwardly facing surface 54 of the mask 12. Each of the first fasteners 52 is positioned adjacent to a distal end 56 of a respective one of the plurality of straps 18. A pair of second fasteners 58 is each attached to the outwardly facing surface 32 of the mask 12 and each of the second fasteners 58 is positioned adjacent to the distal end 56 of a respective one of the plurality of straps 18. Each of the first fasteners 52 is releasably matable to a respective one of the second fasteners 58 to retain the mask 12 on the user's face 14 having the inwardly facing surface 54 abutting the user's face 14. Furthermore, each of the first fasteners 52 and the second fasteners 58 may comprise complementary portions of a hook and loop fastener or other type of multiple use, releasable fastener.

A plurality of heating elements 60 is provided and each of the plurality of heating elements 60 is integrated into the mask 12. Each of the plurality of heating elements 60 is strategically arranged on the mask 12 to facilitate each of the plurality of heating elements 60 to be positioned on a respective one of a left side of the user's jaw 62, a right side of the user's jaw 64 and a front side of the user's jaw 66. Furthermore, each of the plurality of heating elements 60 is in thermal communication with the mask 12 such that the plurality of heating elements 60 heats the mask 12 when the plurality of heating elements 60 is turned on. In this way each of the plurality of heating elements 60 facilitates dental pain to be treated with heat. Additionally, each of the plurality of heating elements 60 is independently actuatable with respect to each other to facilitate the user 14 to apply heat to specific areas of the user's jaw for treating localized dental pain.

Each of the heating elements 60 is positioned between the inwardly facing surface 54 of the mask 12 and the outwardly facing surface 32 of the mask 12. Each of the plurality of heating elements 60 comprises a series of coils 68 that are spaced apart from each other and are distributed between the top edge 38 and a bottom edge 70 of the mask 12. The plurality of heating elements 60 includes a first lateral heating element 72, a second lateral heating element 74 and a front heating element 76; each of the first lateral heating element 72 and the second lateral heating element 74 is positioned between a respective one of the pair of slots 48 and the nose 16.

The front heating element 76 is positioned between each of the first lateral heating element 72 and the second lateral heating element 74 having the front heating element 76 extending between the nose 16 and the bottom edge 70 of the mask 12. Additionally, the front heating element 76 includes a top element 78 that is positioned adjacent to the base 46 of the reuleaux triangle 37 defined by the nose 16. The front heating element 76 includes a bottom element 80 that is spaced downwardly from the top element 78 to accommodate the user's mouth 82 when the user 14 wears the mask 12. Each of the plurality of heating elements 60 may comprise carbon fiber heating panels or other type of electronic heating element that has a minimal thickness to inhibit the user 14 from feeling the heating elements 60 while wearing the mask 12. Additionally, the plurality of heating elements 60 may have an operational temperature ranging between approximately 80.0 degrees fahrenheit to 110.0 degrees fahrenheit.

A conductor 84 is integrated into the mask 12 and the conductor 84 is electrically coupled to each of the plurality of heating elements 60. The conductor 84 extends into the pocket 24 such that a free end 86 of the conductor 84 is exposed. Furthermore, a data plug 88 is electrically coupled to the free end 86 of the conductor 84. The data plug 88 may be a universal serial bus plug or other type of miniature data plug. A personal electronic device 90 is included which stores a control program 92 that can be manipulated by the user 14. The personal electronic device 90 may comprise a smart phone or other similar type of device that has wireless communication capabilities and data storage capabilities. Additionally, the control program 92 may comprise a smart phone application that includes temperature control and the ability to actuate or de-actuate each of the plurality of heating elements 60.

A communication unit 94 is positionable in the pocket 24 on the mask 12 and the communication unit 94 is in communication with each of the plurality of heating elements 60. Additionally, the communication unit 94 is in remote communication with the personal electronic device 90 thereby facilitating the control program 92 to control each of the plurality of heating elements 60. In this way the communication unit 94 facilitates the user 14 to remotely control the plurality of heating elements 60. The communication unit 94 comprises a housing 96 that is insertable into the pocket 24. A data port 98 is recessed into the housing 96 and the data port 98 insertably receives the data plug 88 on the free end 86 of the conductor 84. Furthermore, the data port 98 may comprise a universal serial bus port plug or other type of miniaturized data plug that is matable to the data plug 88.

The communication unit 94 includes a processor 100 that is positioned in the housing 96 and the processor 100 is electrically coupled to the data port 98. The communication unit 94 includes a transceiver 102 that is positioned in the housing 96 and the transceiver 102 is electrically coupled to the processor 100. Furthermore, the transceiver 102 is in wireless communication with the personal electronic device 90 thereby facilitating the transceiver 102 to receive operational commands from the personal electronic device 90. The transceiver 102 may comprise a radio frequency transceiver or the like and the transceiver 102 may employ Bluetooth communication protocols. In this way the transceiver 102 can be linked to a variety of different electronic devices.

The operational commands includes an actuate command and a temperature command; the actuate command and the temperature command is communicated to the processor 100. The processor 100 actuates respective ones of the plurality of heating elements 60 according to the actuate command. In this way the plurality of heating elements 60 can be turned on independently or in any combination. Furthermore, the processor 100 adjusts an operational temperature of the respective heating elements 60 between a minimum temperature and a maximum temperature according to the temperature command. In this way the user 14 could apply heat only to the left side of their jaw, for example, to treat localized dental pain on the left side of their jaw.

The communication unit 94 includes a rechargeable battery 104 that is positioned in the housing 96 and the rechargeable battery 104 is electrically coupled to the processor 100. The rechargeable battery 104 is charged by a charge cord 106 when the charge cord 106 is plugged into the data port 98. The communication unit 94 includes a power button 108 that is movably integrated into the housing 96 and the power button 108 is electrically coupled to the processor 100. The power button 108 alternatively actuates or de-actuates the processor 100 when the power button 108 is depressed.

In use, the user 14 wears the mask 12 and the user 14 synchronizes the personal electronic device 90 with the communication unit 94. In this way the user 14 can control the plurality of heating elements 60 with the personal electronic device 90. Thus, the user 14 can apply heat to a particular area of their jaw to treat dental pain associated with a toothache, for example, or other dental procedure that is typically accompanied by pain and inflammation. Additionally, the temperature of the heating elements 60 can be adjusted between the minimum temperature and the maximum temperature in accordance with the user's 14 preferences. In this way the user 14 can enjoy several hours of comfort with heat being directly and continuously applied to a desired location of their jaw. The communication unit 94 is removed from the pocket 24 and the charge cord 106 is plugged into the data port 98 to charge the rechargeable battery 104 as needed.

With respect to the above description then, it is to be realized that the optimum dimensional relationships for the parts of an embodiment enabled by the disclosure, to include variations in size, materials, shape, form, function and manner of operation, device and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A facial warming device for warming a user's face along their jaw line for treating dental pain, said device comprising:

a mask being wearable on a user's face, said mask having a nose being centrally positioned between a plurality of straps wherein said nose is configured to cover the user's nose and each of said straps is configured to extend around the user's head, said mask having a pocket being attached to said mask;

a plurality of heating elements, each of said plurality of heating elements being integrated into said mask, each of said plurality of heating elements being strategically arranged on said mask wherein each of said plurality of heating elements is configured to be positioned on a respective one of a left side of the user's jaw and a right side of the user's jaw and a front side of the user's jaw, each of said plurality of heating elements being in thermal communication with said mask such that said plurality of heating elements heats said mask when said plurality of heating elements is turned on wherein each of said plurality of heating elements is configured to facilitate dental pain to be treated with heat, each of said plurality of heating elements being independently actuatable with respect to each other wherein said plurality of heating elements is configured to facilitate the user to apply heat to specific areas of the users' jaw for treating localized dental pain;

a personal electronic device storing a control program wherein said control program is configured to be manipulated by the user; and a communication unit being positionable in said pocket on said mask, said communication unit being in communication with each of said plurality of heating elements, said communication unit being in remote said control program to control each of said plurality of heating elements wherein said communication unit is configured to facilitate the user to remotely control said plurality of heating elements.

2. The device according to claim 1, wherein:

said nose has a perimeter edge being attached to an outwardly facing surface of said mask, said perimeter edge having a plurality of sides intersecting each other at a curve such that said nose has the shape of a reuleaux triangle;

said nose curves outwardly from said outwardly facing surface wherein said nose is configured to accommodate the user's nose;

said nose extends downwardly from a top edge of said mask at a point being centrally located between a first lateral edge and a second lateral edge of said mask;

said top edge curves upwardly along each of a pair of legs of said reuleaux triangle having a base of said reuleaux triangle being spaced downwardly from said top edge; and said nose is comprised of a mesh material wherein said nose is configured to facilitate the user to breathe through said nose when the user is wearing said mask.

3. The device according to claim 1, wherein said mask has a pair of slots each extending from a respective one of a first lateral edge and a second lateral edge of said mask toward said nose, each of said slots being centrally positioned along said respective first lateral edge and said second lateral edge such that each of said slots defines a respective pair of said plurality of straps wherein each of said pair of slots is configured to accommodate a respective one of the user's ears when said straps are wrapped around the user's head.

4. The device according to claim 1, further comprising:

a pair of first fasteners, each of said first fasteners being attached to an inwardly facing surface of said mask, each of said first fasteners being positioned adjacent to a distal end of a respective one of said plurality of straps; and a pair of second fasteners, each of said second fasteners being attached to an outwardly facing surface of said mask, each of said second fasteners being positioned adjacent to said distal end of a respective one of said plurality of straps, each of said first fasteners being releasably matable to a respective one of said second fasteners wherein said plurality of straps is configured to retain said mask on the user's face having said inwardly facing surface abutting the user's face.

5. The device according to claim 3, wherein:

each of said heating elements is positioned between an inwardly facing surface of said mask and an outwardly facing surface of said mask, each of said plurality of heating elements comprising a series of coils being spaced apart from each other and being distributed between a top edge and a bottom edge of said mask;

said plurality of heating elements includes a first lateral heating element and a second lateral heating element; and each of said first lateral heating element and said second lateral heating element is positioned between a respective one of said pair of slots and said nose.

6. The device according to claim 2, wherein:

said plurality of heating elements includes a first lateral heating element, a second lateral heating element and a front heating element, said front heating element being positioned between each of said first lateral heating element and said second lateral heating element having said front heating element extending between said nose and a bottom edge of said mask;

said front heating element includes a top element being positioned adjacent to said base of said reuleaux triangle defined by said nose; and said front heating element includes a bottom element being spaced downwardly from said top element wherein said top element and said bottom element are configured to accommodate the user's mouth when the user wears said mask.

7. The device according to claim 1, wherein:

said device includes a conductor being integrated into said mask, said conductor being electrically coupled to each of said plurality of heating elements, said conductor extending into said pocket such that a free end of said conductor is exposed, said conductor having a data plug being electrically coupled to said free end; and said communication unit comprises a housing being insertable into said pocket, said housing having a data port being recessed into said housing, said data port insertably receiving said data plug on said free end of said conductor.

8. The device according to claim 7, wherein said communication unit includes:

a processor being positioned in said housing, said processor being electrically coupled to said data port; and a transceiver being positioned in said housing, said transceiver being electrically coupled to said processor, said transceiver being in wireless communication with said personal electronic device thereby facilitating said transceiver to receive operational commands from said personal electronic device.

9. The device according to claim 8, wherein:

said operational commands includes an actuate command and a temperature command;

said actuate command and said temperature command are communicated to said processor;

said processor actuates respective ones of said plurality of heating elements according to said actuate command; and said processor adjusts an operational temperature of said respective heating elements between a minimum temperature and a maximum temperature according to said temperature command.

10. The device according to claim 8, wherein said communication unit includes:

a rechargeable battery being positioned in said housing, said rechargeable battery being electrically coupled to said processor, said rechargeable battery being charged by a charge cord when the charge cord is plugged into said data port; and a power button being movably integrated into said housing, said power button being electrically coupled to said processor, said power button alternatively actuating or de-actuating said processor when said power button is depressed.

11. A facial warming device for warming a user's face along their jaw line for treating dental pain, said device comprising:

a mask being wearable on a user's face, said mask having a nose being centrally positioned between a plurality of straps wherein said nose is configured to cover the user's nose and each of said straps is configured to extend around the user's head, said mask having a pocket being attached to said mask, said nose having a perimeter edge being attached to an outwardly facing surface of said mask, said perimeter edge having a plurality of sides intersecting each other at a curve such that said nose has the shape of a reuleaux triangle, said nose curving outwardly from said outwardly facing surface wherein said nose is configured to accommodate the user's nose, said nose extending downwardly from a top edge of said mask at a point being centrally located between a first lateral edge and a second lateral edge of said mask, said top edge curving upwardly along each of a pair of legs of said reuleaux triangle having a base of said reuleaux triangle being spaced downwardly from said top edge, said nose being comprised of a mesh material wherein said nose is configured to facilitate the user to breathe through said nose when the user is wearing said mask, said mask having a pair of slots each extending from a respective one of said first lateral edge and said second lateral edge of said mask toward said nose, each of said slots being centrally positioned along said respective first lateral edge and said second lateral edge such that each of said slots defines a respective pair of said plurality of straps wherein each of said pair of slots is configured to accommodate a respective one of the user's ears when said straps are wrapped around the user's head;

a pair of first fasteners, each of said first fasteners being attached to an inwardly facing surface of said mask, each of said first fasteners being positioned adjacent to a distal end of a respective one of said plurality of straps;

a pair of second fasteners, each of said second fasteners being attached to said outwardly facing surface of said mask, each of said second fasteners being positioned adjacent to said distal end of a respective one of said plurality of straps, each of said first fasteners being releasably matable to a respective one of said second fasteners wherein said plurality of straps is configured to retain said mask on the user's face having said inwardly facing surface abutting the user's face;

a plurality of heating elements, each of said plurality of heating elements being integrated into said mask, each of said plurality of heating elements being strategically arranged on said mask wherein each of said plurality of heating elements is configured to be positioned on a respective one of a left side of the user's jaw and a right side of the user's jaw and a front side of the user's jaw, each of said plurality of heating elements being in thermal communication with said mask such that said plurality of heating elements heats said mask when said plurality of heating elements is turned on wherein each of said plurality of heating elements is configured to facilitate dental pain to be treated with heat, each of said plurality of heating elements being independently actuatable with respect to each other wherein said plurality of heating elements is configured to facilitate the user to apply heat to specific areas of the users' jaw for treating localized dental pain, each of said heating elements being positioned between said inwardly facing surface of said mask and said outwardly facing surface of said mask, each of said plurality of heating elements comprising a series of coils being spaced apart from each other and being distributed between said top edge and a bottom edge of said mask, said plurality of heating elements including a first lateral heating element, a second lateral heating element and a front heating element, each of said first lateral heating element and said second lateral heating element being positioned between a respective one of said pair of slots and said nose, said front heating element being positioned between each of said first lateral heating element and said second lateral heating element having said front heating element extending between said nose and said bottom edge of said mask, said front heating element including a top element being positioned adjacent to said base of said reuleaux triangle defined by said nose, said front heating element including a bottom element being spaced downwardly from said top element wherein said top element and said bottom element are configured to accommodate the user's mouth when the user wears said mask;

a conductor being integrated into said mask, said conductor being electrically coupled to each of said plurality of heating elements, said conductor extending into said pocket such that a free end of said conductor is exposed, said conductor having a data plug being electrically coupled to said free end;

a personal electronic device storing a control program wherein said control program is configured to be manipulated by the user; and a communication unit being positionable in said pocket on said mask, said communication unit being in communication with each of said plurality of heating elements, said communication unit being in remote said control program to control each of said plurality of heating elements wherein said communication unit is configured to facilitate the user to remotely control said plurality of heating elements, said communication unit comprising:

a housing being insertable into said pocket, said housing having a data port being recessed into said housing, said data port insertably receiving said data plug on said free end of said conductor;

a processor being positioned in said housing, said processor being electrically coupled to said data port;

a transceiver being positioned in said housing, said transceiver being electrically coupled to said processor, said transceiver being in wireless communication with said personal electronic device thereby facilitating said transceiver to receive operational commands from said personal electronic device, said operational commands including an actuate command and a temperature command, said actuate command and said temperature command being communicated to said processor, said processor actuating respective ones of said plurality of heating elements according to said actuate command, said processor adjusting an operational temperature of said respective heating elements between a minimum temperature and a maximum temperature according to said temperature command;

a rechargeable battery being positioned in said housing, said rechargeable battery being electrically coupled to said processor, said rechargeable battery being charged by a charge cord when the charge cord is plugged into said data port; and a power button being movably integrated into said housing, said power button being electrically coupled to said processor, said power button alternatively actuating or de-actuating said processor when said power button is depressed.

* * * * *